(12) United States Patent
Takasu et al.

(10) Patent No.: US 10,279,376 B2
(45) Date of Patent: May 7, 2019

(54) MEASUREMENT RESULT DISPLAY DEVICE AND MEASUREMENT RESULT DISPLAY METHOD

(71) Applicant: ANRITSU CORPORATION, Kanagawa (JP)

(72) Inventors: Ryota Takasu, Kanagawa (JP); Yasuhiro Miyake, Kanagawa (JP); Soichiro Kai, Kanagawa (JP)

(73) Assignee: ANRITSU CORPORATION, Kanagawa (JP)

( * ) Notice: Subject to any disclaimer, the term of this patent is extended or adjusted under 35 U.S.C. 154(b) by 0 days.

(21) Appl. No.: 15/884,834

(22) Filed: Jan. 31, 2018

(65) Prior Publication Data

US 2018/0236496 A1   Aug. 23, 2018

(30) Foreign Application Priority Data

Feb. 21, 2017   (JP) .................. 2017-029846

(51) Int. Cl.
| | |
|---|---|
| *G01N 21/31* | (2006.01) |
| *B07C 5/342* | (2006.01) |
| *G01N 21/25* | (2006.01) |
| *G01D 3/06* | (2006.01) |
| *G01R 23/17* | (2006.01) |
| *G01D 3/024* | (2006.01) |

(Continued)

(52) U.S. Cl.
CPC .............. *B07C 5/342* (2013.01); *G01D 1/18* (2013.01); *G01D 3/024* (2013.01); *G01D 3/063* (2013.01); *G01D 7/005* (2013.01); *G01D 7/02* (2013.01); *G01J 3/027* (2013.01); *G01J 3/0264* (2013.01); *G01N 21/255* (2013.01); *G01N 21/31* (2013.01); *G01R 23/17* (2013.01); *G01J 2003/2833* (2013.01)

(58) Field of Classification Search
CPC ....... G01N 21/31; G01N 21/255; G01R 23/17
See application file for complete search history.

(56) References Cited

U.S. PATENT DOCUMENTS

| | | | |
|---|---|---|---|
| 2004/0075831 A1* | 4/2004 | Suzuki | G01J 3/12 356/328 |
| 2011/0110658 A1* | 5/2011 | Kojima | G01J 3/28 398/26 |
| 2015/0057977 A1* | 2/2015 | Ishihara | G01J 3/28 702/189 |

OTHER PUBLICATIONS

Tassé, Jean-Sebastien, "Drastically Cutting Down Turn-Up and Repair Time with an Impairment Detection Tool", EXFO Inc., Application Note 273, Dec. 2012, pp. 1-3, Canada.

* cited by examiner

*Primary Examiner* — Jermele M Hollington
*Assistant Examiner* — Alvaro E Fortich
(74) *Attorney, Agent, or Firm* — Pearne & Gordon LLP

(57) ABSTRACT

Provided are a measurement result display device and a measurement result display method which are capable of making a list of how much difference is present between an allowable value and a measurement value of each measurement item measured by a measuring instrument, in a visually discriminable state. An allowable upper limit value indicator 21 and an allowable lower limit value indicator 22 are disposed at display positions which are set in advance in a measurement result image 20 as positions indicating an allowable upper limit value and an allowable lower limit value, and a measurement value indicator 23 is disposed at a display position calculated from display positions of the (Continued)

allowable upper limit value indicator 21 and allowable lower limit value indicator 22 and a measurement value measured by the measurement unit 10.

20 Claims, 10 Drawing Sheets

(51) Int. Cl.
*G01D 1/18* (2006.01)
*G01D 7/00* (2006.01)
*G01D 7/02* (2006.01)
*G01J 3/02* (2006.01)
*G01J 3/28* (2006.01)

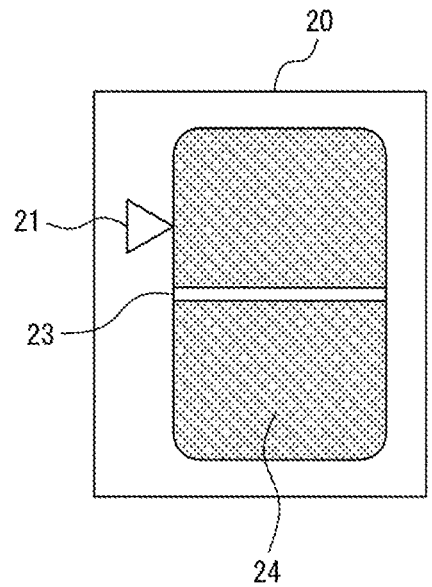
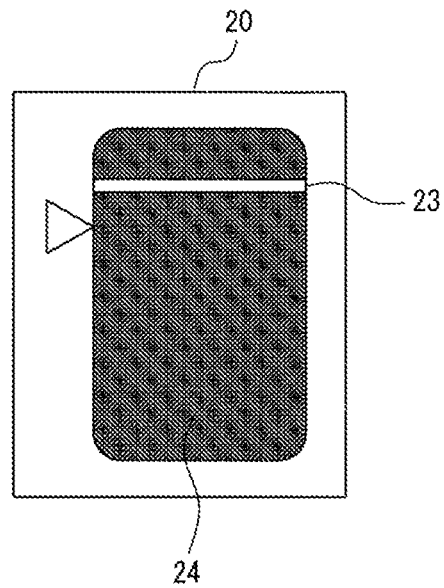
FIG. 6A FIG. 6B
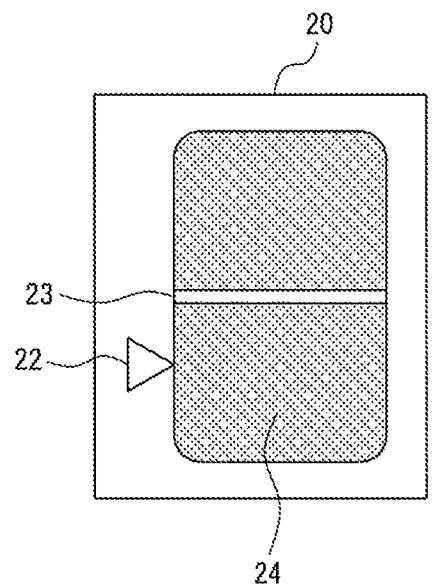
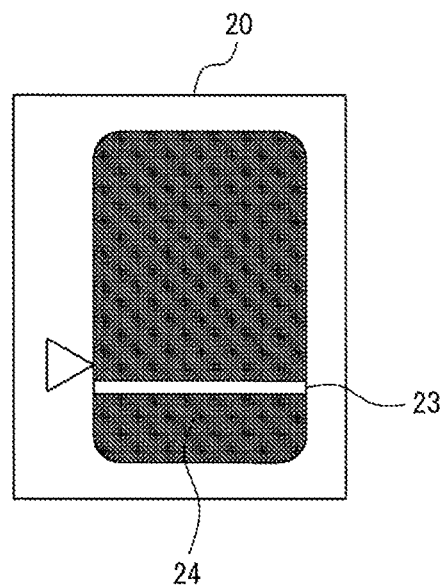
FIG. 6C FIG. 6D

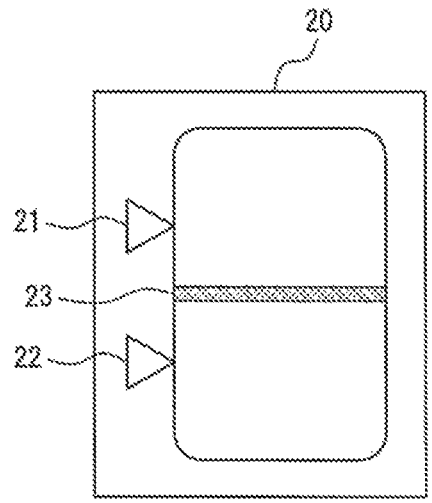 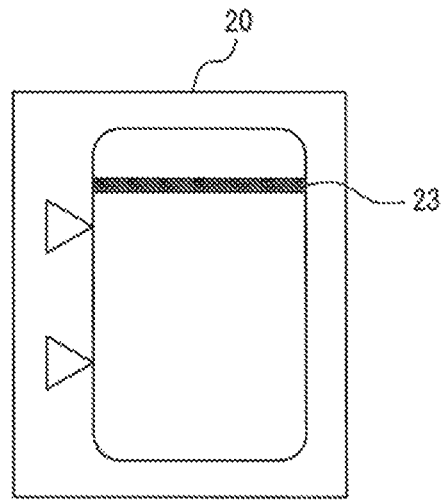
FIG.7A        FIG.7B
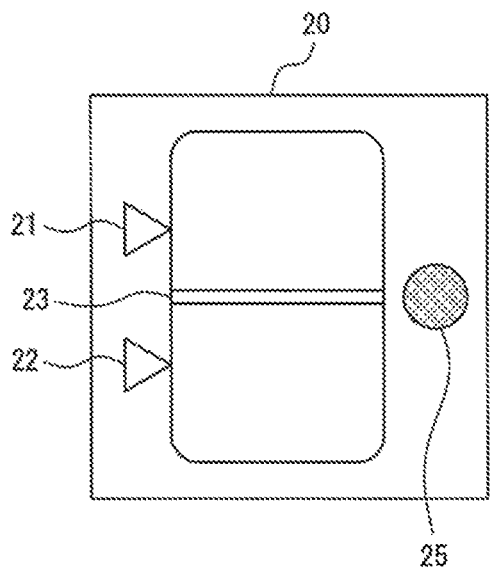 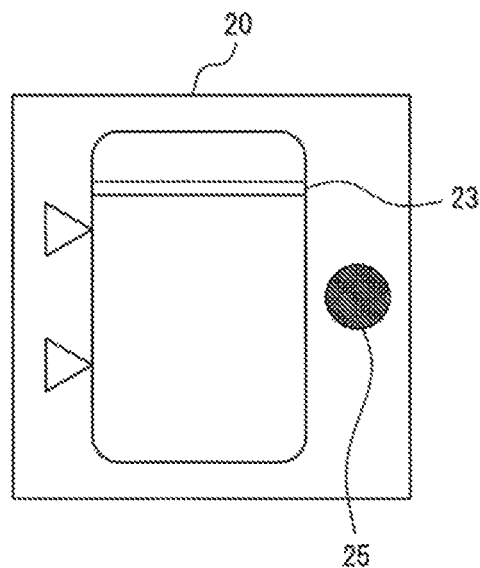
FIG.8A        FIG.8B

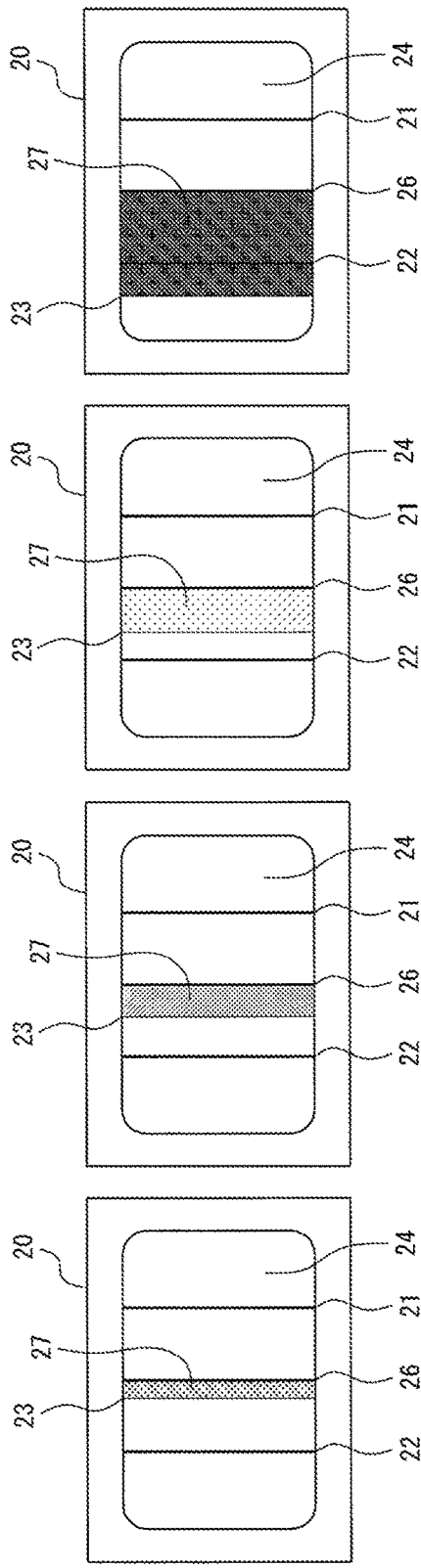

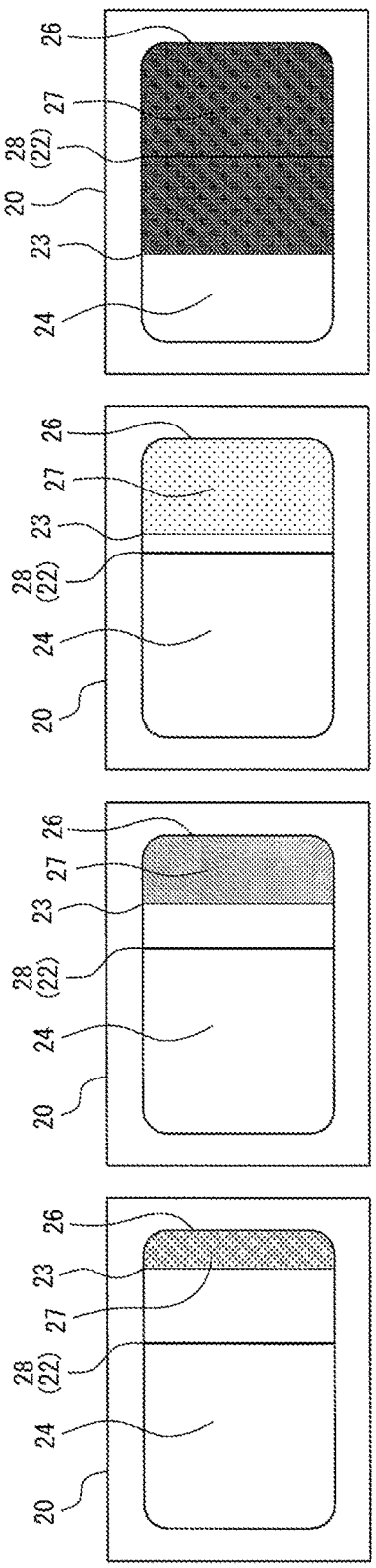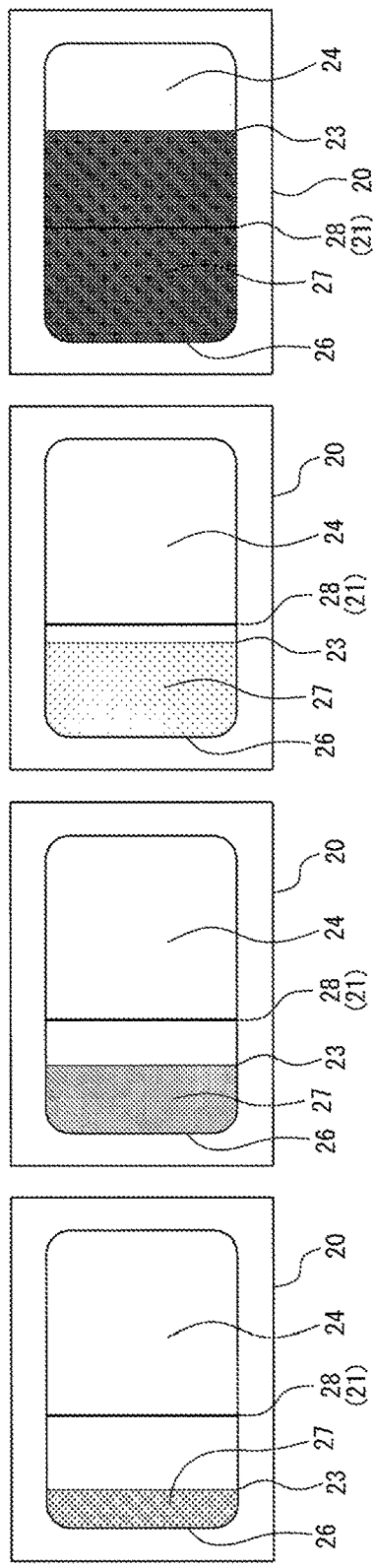

MEASUREMENT RESULT DISPLAY DEVICE AND MEASUREMENT RESULT DISPLAY METHOD

TECHNICAL FIELD

The present invention relates to a measurement result display device and a measurement result display method which are capable of graphically displaying measurement results.

BACKGROUND ART

Hitherto, as disclosed in Non-Patent Document 1, a technique is proposed in which measurement results of a plurality of measurement items are displayed on a display device using icons indicating three states of a state where a measurement value does not exceed a threshold, a state where the measurement value exceeds a threshold but is within a predetermined value, and a state where the measurement value exceeds a threshold and exceeds a predetermined value as well.

RELATED ART DOCUMENT

Non-Patent Document

[Non-Patent Document 1] EXFO Inc., Application Note 273, Drastically Cutting Down Turn-Up and Repair Time with an Impairment Detection Tool, December 2012, pp. 1-3, Canada

DISCLOSURE OF THE INVENTION

Problem that the Invention is to Solve

However, such a related art has a problem in that it is not possible to make a list of how much difference is present between a measurement value of each measurement item measured by a measuring instrument and an allowable value such as a threshold in a discriminable state.

The present invention is contrived in order to solve such a problem, and an object thereof is to provide a measurement result display device and a measurement result display method which are capable of making a list of how much difference is present between a measurement value of each measurement item measured by a measuring instrument and an allowable value in a discriminable state.

Means for Solving the Problem

According to a first aspect of the present invention, there is provided a measurement result display device including: a display control unit (13) that arranges and displays a plurality of measurement result images (20) indicating measurement results of a plurality of measurement items performed by a measuring instrument (10), respectively, on a display device (12); and a storage unit (11) that has an allowable upper limit value and an allowable lower limit value according to the measurement item stored therein, wherein, as the measurement result image, the display control unit displays a frame region (24), an allowable upper limit value indicator (21) and an allowable lower limit value indicator (22) that indicate two predetermined positions which are set within the frame region so as to be separated from each other in a first direction across the frame region, as positions indicating an allowable upper limit value and an allowable lower limit value stored in the storage unit, and a measurement value indicator (23) that indicates a measurement value measured by the measuring instrument, the indicator being displayed at a position to which the measurement value corresponds with respect to the allowable upper limit value indicator and the allowable lower limit value indicator, with the first direction set to a direction of increase or decrease in numerical value.

With such a configuration, in the measurement result display device according to the first aspect of the present invention, the allowable upper limit value indicator and the allowable lower limit value indicator are disposed at display positions which are set in advance in the measurement result image as positions indicating an allowable upper limit value and an allowable lower limit value, and the measurement value indicator is disposed at a display position calculated from the display positions of the allowable upper limit value indicator and the allowable lower limit value indicator, and the measurement value measured by the measuring instrument. Thereby, it is possible to make a list of how much difference is present between an allowable value and the measurement value of each measurement item measured by measuring instrument, in a discriminable state.

In a measurement result display device of second aspect of the present invention according to the measurement result display device of the first aspect of the present invention, in a case where the measurement item has only any one of the allowable upper limit value and the allowable lower limit value, the storage unit has a value separated by a predetermined constant from the one allowable value stored therein as the other allowable value, and the display control unit displays only the allowable upper limit value indicator or only the allowable lower limit value indicator, indicating the one allowable value, on the display device.

With such a configuration, in the measurement result display device of the second aspect of the present invention, it is possible to appropriately dispose the measurement value indicator even in a case of the measurement item having only any one of the allowable upper limit value and the allowable lower limit value.

In a measurement result display device of a third aspect of the present invention according to the measurement result display device of the first aspect of the present invention, the display control unit indicates whether the measurement value is within an allowable range according to the measurement item, with the coloring of the frame region. In addition, in the measurement result display device of a fourth aspect of the present invention according to the measurement result display device of the second aspect of the present invention, the display control unit indicates whether the measurement value is within an allowable range according to the measurement item, with the coloring of the frame region.

With such a configuration, the measurement result display device of the third or fourth aspect of the present invention indicates whether the measurement value measured by the measuring instrument is within an allowable range with the coloring of the frame region, and thus it is possible to recognize whether the measurement value measured by the measuring instrument is within an allowable range.

In a measurement result display device of a fifth aspect of the present invention according to the measurement result display device of the first aspect of the present invention, the display control unit indicates whether the measurement value is within an allowable range according to the measurement item, with the coloring of the measurement value indicator.

With such a configuration, the measurement result display device of the fifth aspect of the present invention indicates whether the measurement value measured by the measuring instrument is within an allowable range with the coloring of the measurement value indicator, and thus it is possible to recognize whether the measurement value measured by the measuring instrument is within an allowable range without occupying the frame region of the measurement result image.

In a measurement result display device of a sixth aspect of the present invention according to the measurement result display device of the first aspect of the present invention, the display control unit further displays a determination result indicator (25) that indicates whether the measurement value is within an allowable range according to the measurement item, as the measurement result image, with coloring, outside of the frame region.

With such a configuration, the measurement result display device of the sixth aspect of the present invention displays the determination result indicator that indicates whether the measurement value measured by the measuring instrument is within an allowable range, with coloring, outside of the frame region, and thus it is possible to recognize whether the measurement value measured by the measuring instrument is within an allowable range without occupying the frame region of the measurement result image.

In a measurement result display device of a seventh aspect of the present invention according to the measurement result display device of the third aspect of the present invention, the display control unit linearly changes the coloring in accordance with a distance between display positions of the allowable upper limit value indicator or the allowable lower limit value indicator and the measurement value indicator.

With such a configuration, in the measurement result display device of the seventh aspect of the present invention, it is possible to visually discriminate a difference between an allowable value and the measurement value of each measurement item measured by the measuring instrument up to a finer level.

In a measurement result display device of an eighth aspect of the present invention according to the measurement result display device of the first aspect of the present invention, as the measurement result image, the display control unit further displays an intermediate value indicator (26) that indicates an intermediate value between the allowable upper limit value and the allowable lower limit value, the indicator being linearly displayed across a substantial center of the frame region, linearly displays the allowable upper limit value indicator and the allowable lower limit value indicator across the frame region at both positions having the intermediate value indicator interposed therebetween, linearly displays the measurement value indicator across the frame region similarly to the intermediate value indicator, and changes a display of a measurement value display region (27) between the intermediate value indicator and the measurement value indicator, in accordance with a distance between display positions of the intermediate value indicator and the measurement value indicator.

With such a configuration, in the measurement result display device of the eighth aspect of the present invention, the intermediate value indicator, and the allowable upper limit value indicator and the allowable lower limit value indicator as positions indicating the allowable upper limit value and the allowable lower limit value are disposed at display positions which are set in advance in the measurement result image, the measurement value indicator is disposed at a display position calculated from the display positions of the allowable upper limit value indicator and the allowable lower limit value indicator and the measurement value measured by the measuring instrument, and the display of the measurement value display region is changed in accordance with a difference between the display positions of the intermediate value indicator and the measurement value indicator. Thereby, it is possible to make a list of how much difference is present between an allowable value and the measurement value of each measurement item measured by measuring instrument, in a discriminable state.

In a measurement result display device of a ninth aspect of the present invention according to the measurement result display device of the eighth aspect of the present invention, the display control unit displays only half of a region on a side where the measurement value display region is present, as the measurement result image.

With such a configuration, the measurement result display device of the ninth aspect of the present invention displays only half of a region of the measurement result image in the measurement result display device of the eighth aspect on a side where the measurement value display region is present, and thus it is possible to make a list of how much difference is present between an allowable value and the measurement value of each measurement item measured by the measuring instrument, in a more finely and visually discriminable state.

In a measurement result display device of a tenth aspect of the present invention according to the measurement result display device of the first aspect of the present invention, the display control unit displays the measurement value indicator across the frame region in a second direction intersecting the first direction.

With such a configuration, in the measurement result display device of the tenth aspect of the present invention, the measurement value indicator can be intuitively recognized by an operator.

In a measurement result display device of an eleventh aspect of the present invention according to the measurement result display device of the first aspect of the present invention, the display control unit displays the frame region in a rectangular shape, or displays the frame region in a fan shape having a deformed rectangle.

With such a configuration, in the measurement result display device of the eleventh aspect of the present invention, the frame region can be intuitively recognized by an operator.

In a measurement result display device of a twelfth aspect of the present invention according to the measurement result display device of the first aspect of the present invention, the display control unit arranges and displays the plurality of measurement result images in a lattice shape. In addition, in a measurement result display device of a thirteenth aspect of the present invention according to the measurement result display device of the second aspect of the present invention, the display control unit arranges and displays the plurality of measurement result images in a lattice shape. In addition, in a measurement result display device of a fourteenth aspect of the present invention according to the measurement result display device of the third aspect of the present invention, the display control unit arranges and displays the plurality of measurement result images in a lattice shape. In addition, in a measurement result display device of a fifteenth aspect of the present invention according to the measurement result display device of the fourth aspect of the present invention, the display control unit arranges and displays the plurality of measurement result images in a lattice shape. In addition, in a measurement result display device of a sixteenth aspect of the present invention according to the measurement result display device of the fifth aspect of the present invention, the display control unit arranges and displays the plurality of measurement result images in a lattice shape. In addition, in a measurement result display device of a seventeenth aspect of the present invention according to the measurement result display device of the sixth aspect of the present invention, the display control unit arranges and displays the plurality of measurement result images in a lattice shape. In addition, in a measurement result display device of an eighteenth aspect of the present invention according to the measurement result display device of the eighth aspect of the present invention, the display control unit arranges and displays the plurality of measurement result images in a lattice shape. In addition, in a measurement result display device of a nineteenth aspect of the present invention according to the measurement result display device of the ninth aspect of the present invention, the display control unit arranges and displays the plurality of measurement result images in a lattice shape.

With such a configuration, the measurement result display device of any one of the twelfth to nineteenth aspects of the present invention arranges and displays a plurality of measurement result images of a plurality of measurement items in a lattice shape, and thus it is possible to notice the entire measurement results in perspective.

In addition, according to the present invention, there is provided a measurement result display method using a measurement result display device including a display control unit (13) that arranges and displays a plurality of measurement result images (20) indicating measurement results of a plurality of measurement items performed by a measuring instrument (10), respectively, on a display device (12), and a storage unit (11) that has an allowable upper limit value and an allowable lower limit value according to the measurement item stored therein, the method including causing the display control unit to display the measurement result image in the following steps of: displaying a frame region (24); displaying an allowable upper limit value indicator (21) and an allowable lower limit value indicator (22) that indicate two predetermined positions which are set within the frame region so as to be separated from each other in a first direction across the frame region, as positions indicating the allowable upper limit value and the allowable lower limit value stored in the storage unit; and displaying a measurement value indicator (23) that indicates a measurement value measured by the measuring instrument, the indicator being displayed at a position to which the measurement value corresponds with respect to the allowable upper limit value indicator and the allowable lower limit value indicator, with the first direction set to a direction of increase or decrease in numerical value.

In this manner, in the measurement result display method of the present invention, the allowable upper limit value indicator and the allowable lower limit value indicator are disposed at display positions which are set in advance in the measurement result image as positions indicating an allowable upper limit value and an allowable lower limit value, and the measurement value indicator is disposed at a display position calculated from the display positions of the allowable upper limit value indicator and the allowable lower limit value indicator, and the measurement value measured by the measuring instrument. Thereby, it is possible to make a list of how much difference is present between an allowable value and the measurement value of each measurement item measured by measuring instrument, in a visually discriminable state.

Advantage of the Invention

The present invention can provide a measurement result display device and a measurement result display method which are capable of making a list of how much difference is present between an allowable value and a measurement value of each measurement item measured by a measuring instrument, in a visually discriminable state.

BRIEF DESCRIPTION OF THE DRAWINGS

FIGS. 6A to 6D are schematic diagrams illustrating a fourth example of measurement result images displayed on the optical spectrum analyzer device according to the embodiment of the present invention.

FIGS. 7A and 7B are schematic diagrams illustrating a fifth example of measurement result images displayed on the optical spectrum analyzer device according to the embodiment of the present invention.

FIGS. 8A and 8B are schematic diagrams illustrating a sixth example of measurement result images displayed on the optical spectrum analyzer device according to the embodiment of the present invention.

FIGS. 10A to 10D are schematic diagrams illustrating an eighth example of measurement result images displayed on the optical spectrum analyzer device according to the embodiment of the present invention.

FIGS. 11A to 11H are schematic diagrams illustrating a ninth example of measurement result images displayed on the optical spectrum analyzer device according to the embodiment of the present invention.

BEST MODE FOR CARRYING OUT THE INVENTION

Hereinafter, an embodiment of the present invention will be described with reference to the accompanying drawings. Meanwhile, in the present embodiment, an example in which a measurement result display device of the present invention is applied to an optical spectrum analyzer device will be described.

Figure 1:
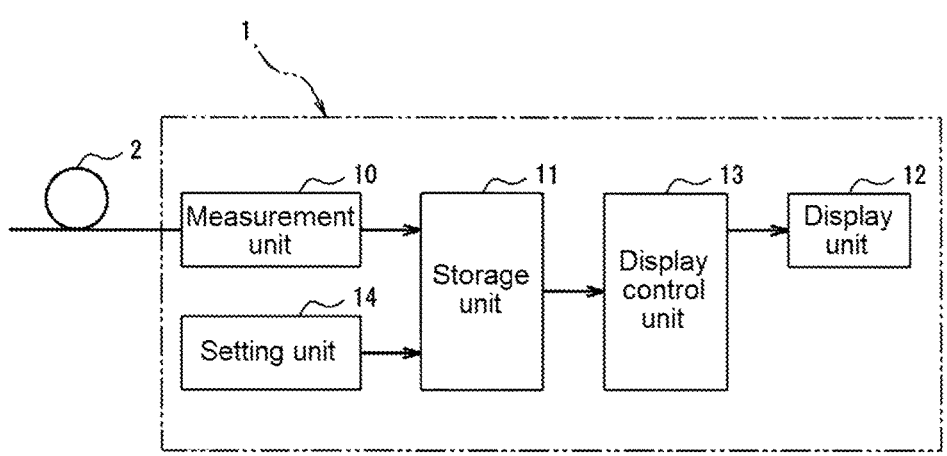
FIG. 1 is a block diagram of an optical spectrum analyzer device according to an embodiment of the present invention.

As shown in FIG. 1, an optical spectrum analyzer device 1 is configured to include a measurement unit 10 as a measuring instrument that measures various types of measurement items of optical signals which are input through an optical cable 2, a storage unit 11 in which allowable upper limit values and allowable lower limit values according to the measurement items of the measurement unit 10 are stored, a display unit 12 as a display device, a display control unit 13 that arranges and displays a plurality of measurement result images indicating the measurement results of a plurality of measurement items performed by the measurement unit 10, respectively, on the display unit 12, and a setting unit 14 that sets the measurement items, the allowable upper limit values and the allowable lower limit values according to the respective measurement items stored in the storage unit 11, and the like.

The optical spectrum analyzer device 1 in the present embodiment is constituted by a computer device (not shown) provided with an optical module for acquiring the spectrum waveform of an optical signal which is input through the optical cable 2. This computer device includes a central processing unit (CPU), a read only memory (ROM), a random access memory (RAM), and a non-volatile recording medium such as a hard disk device or a flash memory.

A program for causing the computer device to function as the optical spectrum analyzer device 1 is stored in the ROM and the non-volatile recording medium of this computer device. That is, the CPU executes the program stored in the ROM and the non-volatile recording medium using the RAM as a work area, and thus the computer device functions as the optical spectrum analyzer device 1.

In the present embodiment, the measurement unit 10 and the display control unit 13 are constituted by a CPU. Meanwhile, the measurement unit 10 may be constituted by other devices such as a field-programmable gate array (FPGA) or an integrated circuit.

The storage unit 11 is constituted by a recording medium such as a RAM or a non-volatile recording medium. The display unit 12 is constituted by a display device provided integrally with or detachably from the computer device. The setting unit 14 is constituted by an input device such as a keyboard device or a pointing device provided integrally with or detachably from the computer device.

The measurement unit 10 is configured to perform a measurement on an optical signal which is input through the optical cable 2 by sweeping and analyzing, for each wavelength ($\lambda$), the measurement values of various types of measurement items such as "Power" (power level [dBm] of an optical signal), "OSNR" (Optical Signal to Noise Ratio, signal/noise ratio [dB]), "Noise" (power level [dBm] of noise), "$\Delta\lambda$" (shift amount [nm] of a wavelength), and "BW 3 dB" (wavelength width [nm] of a 3 dB lower level from the maximum value of power), and to store the measurement values of various types of measurement items in a recording medium or the like constituting the storage unit 11.

Allowable values such as allowable upper limit values and allowable lower limit values according to various types of measurement items are stored in the storage unit 11. Here, there are measurement items for which allowable upper limit values or allowable lower limit value are not specified, as allowable values, depending on measurement items.

For example, "OSNR" is configured such that an allowable lower limit value is specified, but an allowable upper limit value is not specified. Reversely, "BW 3 dB" is configured such that an allowable upper limit value is specified, but an allowable lower limit value is not specified. Therefore, flags indicating whether allowable upper limit values and allowable lower limit values of various types of measurement items are valid are stored in the storage unit 11.

Meanwhile, since allowable upper limit values and allowable lower limit values according to various types of measurement items are referred to by the display control unit 13 as described later, these values are stored in the storage unit 11 regardless of whether being valid.

For example, in a case where an allowable upper limit value is valid and an allowable lower limit value is invalid, a value obtained by subtracting a constant according to a measurement item from the allowable upper limit value is stored as the allowable lower limit value in the storage unit 11. In addition, in an allowable upper limit value is invalid and an allowable lower limit value is valid, a value obtained by adding a constant according to a measurement item to the allowable lower limit value is stored as the allowable upper limit value in the storage unit 11.

Meanwhile, allowable upper limit values and allowable lower limit values according to various types of measurement items, and flags indicating whether the allowable upper limit values and the allowable lower limit values are valid may be able to be selected from a plurality of presets stored in a non-volatile recording medium or the like by the setting unit 14, or may be able to be individually input therefrom.

Figure 2:
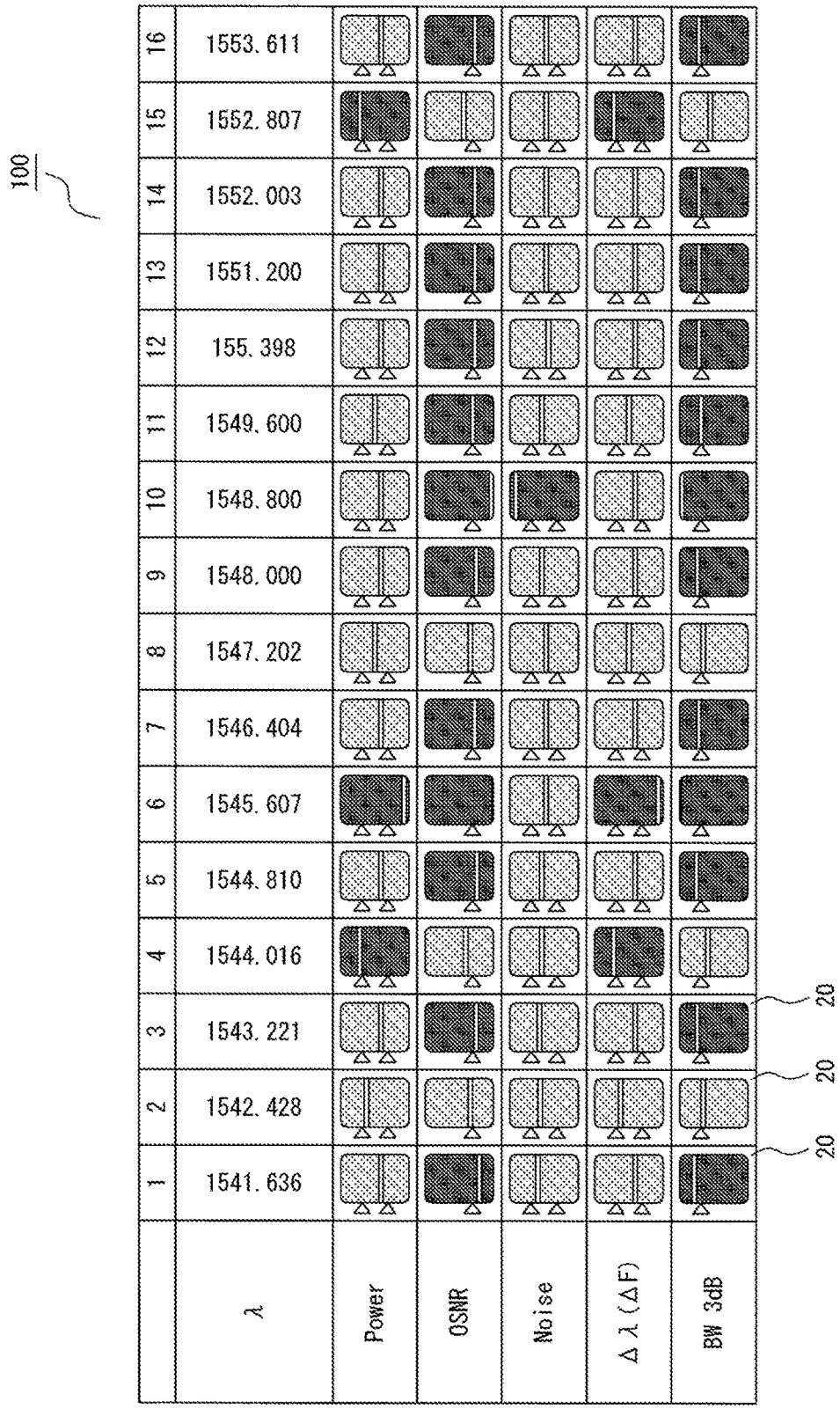
FIG. 2 is a diagram illustrating a list display of measurement result images displayed on the optical spectrum analyzer device according to the embodiment of the present invention.

For example, as shown in FIG. 2, the display control unit 13 is configured to arrange a plurality of measurement result images 20 indicating the measurement results of a plurality of measurement items, respectively, stored in the storage unit 11 or the like on the display unit 12 in a lattice shape with the same size to display the arranged images in a form of a measurement result image list 100. Here, the longitudinal direction represents various types of measurement items, and the traverse direction represents a list at $\lambda$. Meanwhile, the following description is given using one measurement result image 20 of the measurement result image list 100.

Figure 3:
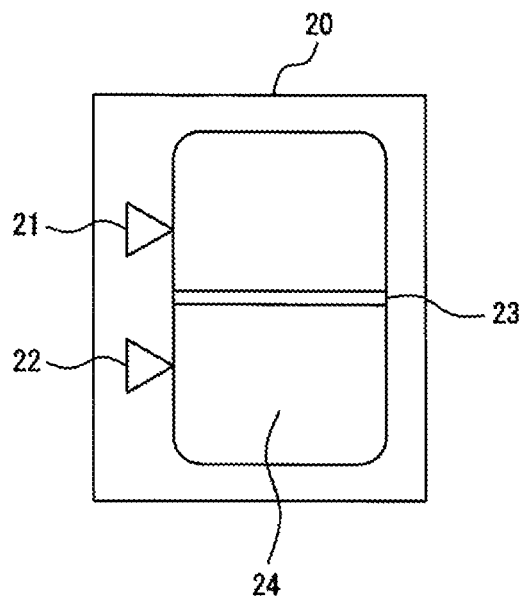
FIG. 3 is a schematic diagram illustrating a first example of a measurement result image displayed on the optical spectrum analyzer device according to the embodiment of the present invention.

As shown in FIG. 3, each of the measurement result images 20 includes a displayable region 24 as a frame-like region mainly indicating a measurement result, an allowable upper limit value indicator 21 and an allowable lower limit value indicator 22 indicating an allowable upper limit value and an allowable lower limit value, respectively, stored in the storage unit 11 in accordance with a measurement item, and a measurement value indicator 23 indicating a measurement value measured by the measurement unit 10.

The display control unit 13 disposes the allowable upper limit value indicator 21 and the allowable lower limit value indicator 22 at display positions which are set in advance in the measurement result image 20. The display positions of the allowable upper limit value indicator 21 and the allowable lower limit value indicator 22 are common between each of the measurement result images 20. In addition, the display control unit 13 disposes the measurement value indicator 23 at a display position which is calculated from the allowable upper limit value and the allowable lower limit value, the display positions of the allowable upper limit value indicator 21 and the allowable lower limit value indicator 22, and the measurement value measured by the measurement unit 10.

That is, the display control unit 13 disposes the measurement value indicator 23 at a display position relative to the display positions of the allowable upper limit value indicator 21 and the allowable lower limit value indicator 22. Specifically, in a case where the allowable upper limit value is set to Vu, the allowable lower limit value is set to Vb, the display position of the allowable upper limit value indicator 21 is set to Yu, the display position of the allowable lower limit value indicator 22 is set to Yb (here, the display position indicates a position in the longitudinal direction of the displayable region 24; the same is true of the following Ym), and the measurement value measured by the measurement unit 10 is set to Vm, the display control unit 13 calculates a display position Ym of the measurement value indicator 23 in accordance with the following expression.

$$Ym=\{(Vm-Vb)/(Vu-Vb)\}\times(Yu-Yb)+Yb$$

That is, with the longitudinal direction of the displayable region 24 estimated as the axial direction of one-dimensional graph, the measurement value indicator 23 is displayed at a position relative to the display positions of the allowable upper limit value indicator 21 and the allowable lower limit value indicator 22.

As shown in FIG. 3, in a case of an aspect in which a position indicated by each indicator of the allowable upper limit value indicator 21, the allowable lower limit value indicator 22 and the measurement value indicator 23 can be definitely discriminated, the display control unit 13 may display each indicator in any aspect of a line, an arrow, a polygon, or the like. For example, in FIG. 3, the display control unit 13 displays the allowable upper limit value indicator 21 and the allowable lower limit value indicator 22 with triangles outside of the displayable region 24, and displays the measurement value indicator 23 with a line having a predetermined width.

Figure 4:
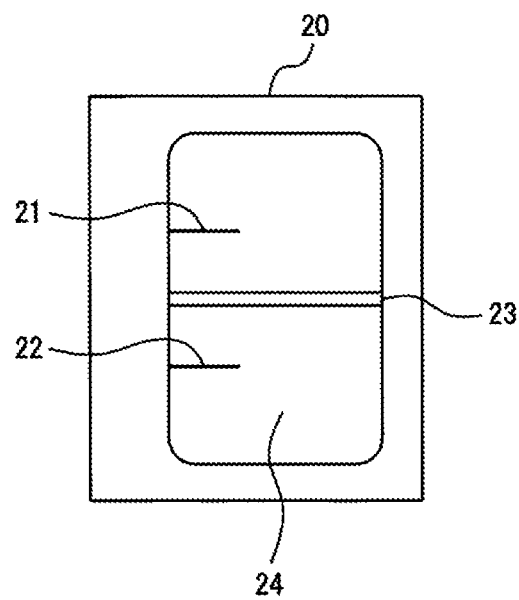
FIG. 4 is a schematic diagram illustrating a second example of a measurement result image displayed on the optical spectrum analyzer device according to the embodiment of the present invention.

On the other hand, for example, as shown in FIG. 4, the display control unit 13 may display the allowable upper limit value indicator 21 and the allowable lower limit value indicator 22 with lines, respectively, within the displayable region 24.

Figure 5A:
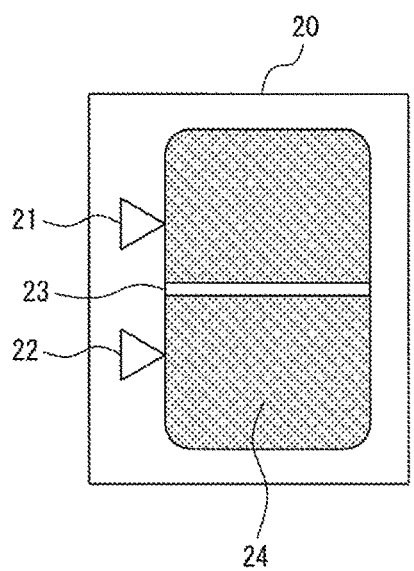
FIGS. 5A and 5B are schematic diagrams illustrating a third example of measurement result images displayed on the optical spectrum analyzer device according to the embodiment of the present invention.
Figure 5B:
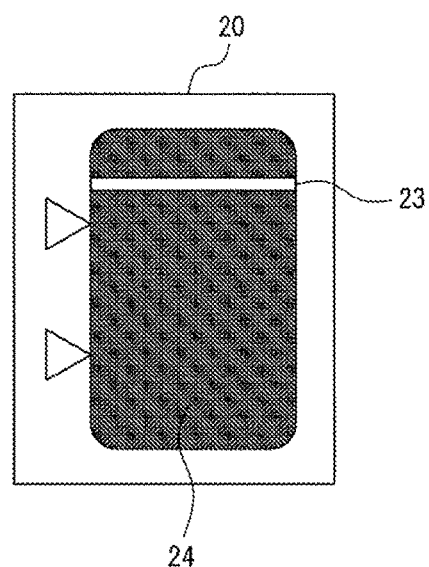

The display control unit 13 indicates whether the measurement value measured by the measurement unit 10 is within an allowable range according to a measurement item with the coloring of the displayable region 24 of the measurement value indicator 23. For example, as shown in FIG. 5A and FIG. 5B, the display control unit 13 colors the displayable region 24 with green as an implication indicating OK in a case where the measurement value measured by the measurement unit 10 is within an allowable range (FIG. 5A), and colors the displayable region 24 with red as an implication indicating a warning in a case where the measurement value is not within an allowable range (FIG. 5B).

Here, the display control unit 13 specifies allowable ranges according to various types of measurement items on the basis of allowable upper limit values and allowable lower limit values stored in the storage unit 11 with respect to respective measurement results and flags indicating whether allowable upper limit values and allowable lower limit values of various types of measurement items are valid.

That is, in a case where each flag indicates that the allowable upper limit value and the allowable lower limit value are valid, the display control unit 13 sets a range between the allowable upper limit value and the allowable lower limit value to an allowable range. In a case where each flag indicates that the allowable upper limit value is valid and the allowable lower limit value is not valid, the display control unit 13 sets a range equal to or less than the allowable upper limit value to an allowable range. In a case where each flag indicates that the allowable upper limit value is not valid and the allowable lower limit value is valid, the display control unit 13 sets a range equal to or greater than the allowable lower limit value to an allowable range.

In association therewith, in a case where any one of the allowable upper limit value and the allowable lower limit value is an allowable value which is not valid, the display control unit 13 does not display the indicator 21 or 22 indicating an allowable value which is not valid of the allowable upper limit value or the allowable lower limit value on the display unit 12.

Specifically, in a case where each flag indicates that the allowable upper limit value is valid and the allowable lower limit value is not valid, as shown in FIG. 6A and FIG. 6B, the display control unit 13 sets the allowable upper limit value indicator 21 to be in a display state, and sets the allowable lower limit value indicator 22 to be in a non-display state. Meanwhile, the diagrams of the drawing indicate the states of OK and a warning, respectively, similarly to FIG. 5.

In a case where each flag indicates that the allowable upper limit value is not valid and the allowable lower limit value is valid, as shown in FIG. 6C and FIG. 6D, the display control unit 13 sets the allowable upper limit value indicator 21 to be in a non-display state, and sets the allowable lower limit value indicator 22 to be in a display state. Similarly, these diagrams indicate the states of OK and a warning, respectively.

In addition, as shown in FIG. 7A and FIG. 7B, the display control unit 13 may indicate whether the measurement value measured by the measurement unit 10 is within an allowable range according to a measurement item with the coloring of the measurement value indicator 23 instead of color display in the entire displayable region 24. Similarly, these diagrams indicate the states of OK and a warning, respectively.

Further, as shown in FIG. 8A and FIG. 8B, the display control unit 13 may cause each of the measurement result images 20 to further include a determination result indicator 25, and indicate whether the measurement value measured by the measurement unit 10 is within an allowable range according to a measurement item with the coloring of the determination result indicator 25 instead of color display in the entire displayable region 24. Similarly, these diagrams indicate the states OK and a warning, respectively.

Figure 9:
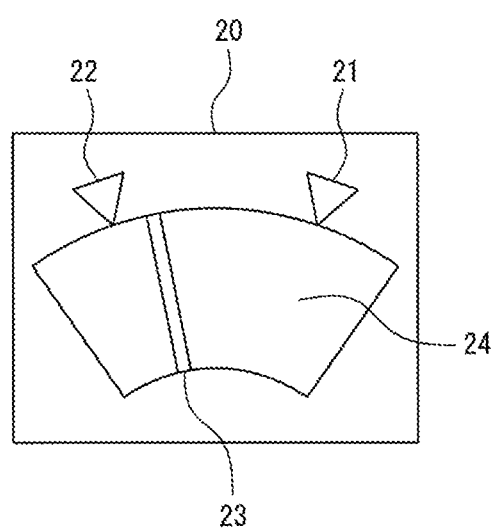
FIG. 9 is a schematic diagram illustrating a seventh example of a measurement result image displayed on the optical spectrum analyzer device according to the embodiment of the present invention.

Meanwhile, the displayable region 24 indicated by the measurement value indicator 23 is not limited to a rectangle as shown in FIGS. 3 to 8. For example, as shown in FIG. 9, the displayable region 24 may be disposed in a traverse direction and be formed in a fan shape deformed from a rectangle. This is true of an embodiment described later.

Meanwhile, color display of the displayable region 24, the measurement value indicator 23, and the determination result indicator 25 may be linearly changed as in an embodiment described later.

In the above description, the display control unit 13 makes a list of how much difference is present between the measurement value of each measurement item and the allowable upper limit value and the allowable lower limit value, with respect to the measurement results of a plurality of measurement items, depending on the display positions of the allowable upper limit value indicator 21, the allowable lower limit value indicator 22 and the measurement value indicator 23, but may make a list of how much difference is present between the measurement value of each measurement item and the allowable upper limit value and the allowable lower limit value, depending on the coloring of a specific region of the measurement result image 20.

For example, as shown in FIGS. 10A to 10D, the display control unit 13 disposes the displayable region 24 in a traverse direction, and further disposes an intermediate value indicator 26 indicating an intermediate value between the allowable upper limit value and the allowable lower limit value stored in the storage unit 11 in accordance with a measurement item, at a position which is set in advance, specifically, an intermediate position between the allowable upper limit value indicator 21 and the allowable lower limit value indicator 22. Each indicator is displayed in a linear shape running across the displayable region 24 in a longitudinal direction, and a measurement value display region 27 is colorized which is a region interposed between the intermediate value indicator 26 and the measurement value indicator 23.

The display control unit 13 linearly changes the coloring of the measurement value display region 27 in accordance with a distance between the display positions of the intermediate value indicator 26 and the measurement value indicator 23. That is, with the traverse direction of the displayable region 24 estimated as the axial direction of one-dimensional graph, the measurement value indicator 23 is displayed at a position relative to the display positions of the allowable upper limit value indicator 21 and the allowable lower limit value indicator 22, and the color of the region (measurement value display region 27) interposed between the intermediate value indicator 26 and the measurement value indicator 23 is further changed with the display position of the measurement value indicator 23.

For example, the display control unit 13 colors the measurement value display region 27 with green in a case where a distance between the display positions of the intermediate value indicator 26 and the measurement value indicator 23 is close to 0, and colors the measurement value display region 27 so as to change gradually from green to yellow as the distance between the display positions of the intermediate value indicator 26 and the measurement value indicator 23 increases.

Specifically, the measurement value display region 27 is colored with RGB=(0, 255, 0) in a case where the distance between the display positions of the intermediate value indicator 26 and the measurement value indicator 23 is close to 0, an R component of the measurement value display region 27 is set in accordance with the distance between the display positions of the intermediate value indicator 26 and the measurement value indicator 23, and the measurement value display region 27 is colored with RGB=(255, 255, 0) in a case where the distance between the display positions of the measurement value indicator 23 and the allowable upper limit value indicator 21 or the allowable lower limit value indicator 22 arrives at 0.

FIGS. 10A to 10D show an aspect in which the distance between the display positions of the intermediate value indicator 26 and the measurement value indicator 23 increases gradually from FIG. 10A toward FIG. 10D. The measurement value display region 27 is colored with green in a case where the distance is close to 0 (FIG. 10A), the measurement value display region 27 changes gradually yellowish green→yellow in a case where the distance increases gradually (FIG. 10B→FIG. 10C), and the measurement value display region 27 changes in color to red in a case where the distance further increases to exceed the allowable lower limit value indicator 22 (FIG. 10D).

Meanwhile, it goes without saying that a color component changed linearly may be other color components without being limited to those described above. In addition, other elements such as brightness or chroma may be changed.

In a case where the measurement value measured by the measurement unit 10 is not within an allowable range according to a measurement item, it is preferable that the display control unit 13 colors the measurement value display region 27 so that the measurement value is different greatly from that in a case of being within an allowable range, that is, an operator easily identifies that the measurement value is outside of a range. For example, in the above-described example, in a case where the measurement value measured by the measurement unit 10 is not within an allowable range, the display control unit 13 colors the measurement value display region 27 with red, that is, RGB=(255, 0, 0).

In addition, in the present embodiment, an example has been described in which the display control unit 13 gradually changes a specific color component (R component in the above-described example) of the coloring of the measurement value display region 27 in accordance with the distance between the display positions of the intermediate value indicator 26 and the measurement value indicator 23, but the display control unit may stepwise change the color component in accordance with the distance between the display positions of the intermediate value indicator 26 and the measurement value indicator 23. For example, the display region may be colored with green in a case where the measurement value indicator 23 is in the vicinity of the intermediate value indicator 26, yellowish green in a case where the measurement value indicator is in the vicinity of the allowable upper limit value indicator 21 or the allowable lower limit value indicator 22, yellow immediately before the measurement value indicator arrives at the allowable upper limit value indicator 21 or the allowable lower limit value indicator 22, and red after the arrival.

Meanwhile, in the present embodiment, in a case where a relation of measurement value=intermediate value is established and the measurement value display region 27 is not generated, a line thicker than that of the intermediate value indicator 26 is displayed behind the intermediate value indicator 26, and the thick line may be displayed with green and be recognized.

In the above description, the display control unit 13 displays the measurement result image 20 including both the allowable upper limit value indicator 21 and the allowable lower limit value indicator 22 indicating an allowable upper limit value and an allowable lower limit value, on the display unit 12. However, the measurement value measured by the measurement unit 10 is necessarily further biased to either the allowable upper limit value side or the allowable lower limit value side than to the intermediate value (however, a case of measurement value=intermediate value is excluded).

Therefore, as shown in FIGS. 11A to 11H, the display control unit 13 may display a measurement result image 20 including an allowable value indicator 28 indicating any of the allowable upper limit value and the allowable lower limit value stored in the storage unit 11 in accordance with a measurement item, the intermediate value indicator 26, and the measurement value indicator 23, on the display unit 12. That is, in the aspect of description in FIGS. 10A to 10D, only a biased side is displayed.

In addition, FIGS. 11A to 11D are an aspect in which only allowable lower limit value sides are displayed. In this case, the right side of the displayable region 24 forms the intermediate value indicator 26. The allowable value indicator 28 as the allowable lower limit value indicator 22 is displayed at a position separated by a predetermined distance from this right side. From (a1) toward (a4), a state is shown in which the measurement value increases gradually in a negative direction. In other words, the width of the measurement value display region 27 increases gradually in a left direction with the right side as a reference position set to a starting point.

On the other hand, FIGS. 11E to 11H are an aspect in which only allowable upper limit value sides are displayed. In this case, the left side of the displayable region 24 forms the intermediate value indicator 26. The allowable value indicator 28 as the allowable upper limit value indicator 21 is displayed at a position separated by a predetermined distance from this left side. From (b1) toward (b4), a state is shown in which the measurement value increases gradually in a positive direction.

The position of the measurement value indicator 23 is determined from the measurement value and the positions of the intermediate value indicator 26 (right side or left side) and the allowable value indicator 28, in the same viewpoint as that in the above-described embodiment.

In a display example shown in FIGS. 11A to 11H, similarly to the example shown in FIGS. 10A to 10D, the display control unit 13 determines the coloring of the measurement value display region 27 between the intermediate value indicator 26 and the measurement value indicator 23, in accordance with the difference between the display positions of the intermediate value indicator 26 and the measurement value indicator 23.

Meanwhile, in the present embodiment, in a case where a relation of measurement value=intermediate value is established and the measurement value display region 27 does not occur, a line thicker than the right side or the left side which is the intermediate value indicator 26 is displayed behind the side, and the thick line may be displayed with green.

Figure 12C:
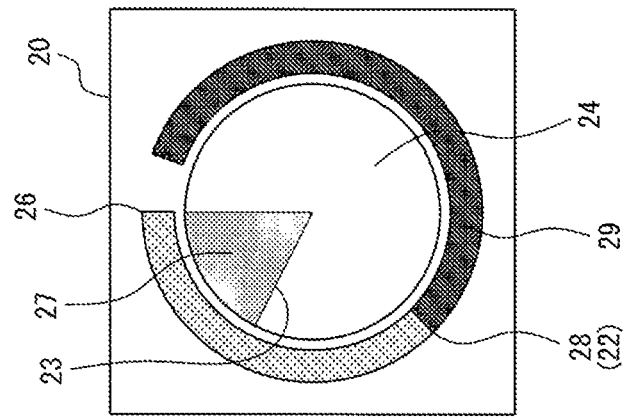
FIGS. 12A to 12C are schematic diagrams illustrating a tenth example of measurement result images displayed on the optical spectrum analyzer device according to the embodiment of the present invention.
Figure 12B:
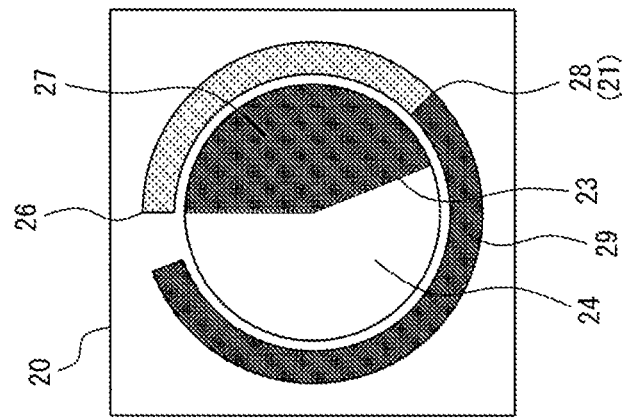
Figure 12A:
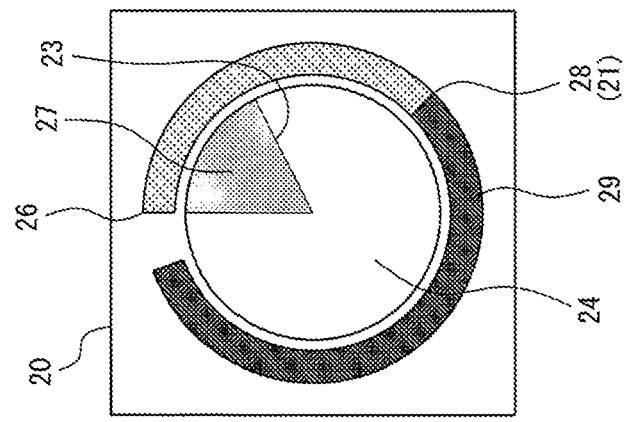

A modification aspect of the aspect of FIGS. 11A to 11H is shown in FIGS. 12A to 12C. In the present aspect, the displayable region 24 is formed in a circular shape, and an encircling line region 29 surrounding this displayable region 24 is newly provided. This encircling line region 29 has a predetermined width in a direction away from the center of a circle.

In addition, FIGS. 12A and 12B are an aspect in which allowable upper limit value sides are displayed. The measurement value display region 27 is formed so that increase or decrease is displayed in a circular graph shape, and increases or decreases in its width clockwise from the radius position of twelve o'clock. The starting-point terminal of the encircling line region 29 is disposed in conformity to the starting-point position of the measurement value display region 27, and this forms the intermediate value indicator 26. A delimiter is provided at a position separated by a predetermined distance at a predetermined angle in a circumferential direction from the intermediate value indicator 26, and this forms the allowable value indicator 28 as the allowable upper limit value indicator 21.

The end-point terminal of the encircling line region 29 extends just before arrival at the whole circumference of the displayable region 24. A space is present from the position of twelve o'clock to the left side, and thus it can be understood that FIGS. 12A and 12B are an aspect in which allowable upper limit value sides are displayed. In addition, FIG. 12C is an aspect in which an allowable lower limit value side is displayed. In this case, a display symmetrical to FIGS. 12A and 12B is shown. Similarly to the aspect of FIGS. 11A to 11H, the display of the measurement value display region 27 changes depending on the distance (distance on the circumference of a circle in this case) between the measurement value indicator 23 which is a movement terminal of the measurement value display region 27 and the intermediate value indicator 26.

Meanwhile, in the present embodiment, in a case where a relation of measurement value=intermediate value is established and the measurement value display region 27 is not generated, a radius position to be a starting point of the measurement value display region 27 is displayed by a thick line and the thick line may be displayed with green.

In addition, the display control unit 13 may cause each of the measurement result images 20 shown in FIGS. 3 to 8 to include a character string indicating the measurement value measured by the measurement unit 10.

In addition, a measurement result display method in all the embodiments includes a display control step, and the display control step is executed by the display control unit 13.

In addition, in all the embodiments, all the measurement result images 20 constituting the measurement result image list 100 as shown in FIG. 2 are not required to have the same size. The same size is preferable in the meaning of an overview of the entirety thereof, but there is no restriction on a change such as a great display of an important measurement item.

As described above, in one of the present embodiments, the allowable upper limit value indicator 21 and the allowable lower limit value indicator 22 are disposed at display positions which are set in advance in the measurement result image 20 as positions indicating an allowable upper limit value and an allowable lower limit value, and the measurement value indicator 23 is disposed at a display position calculated from the display positions of the allowable upper limit value indicator 21 and the allowable lower limit value indicator 22 and the measurement value measured by the measurement unit 10. Thereby, it is possible to make a list of how much difference is present between an allowable value and the measurement value of each measurement item measured by the measuring instrument 10 in a discriminable state.

In addition, in one of the present embodiments, whether the measurement value measured by the measurement unit 10 is within an allowable range is indicated by the coloring of the displayable region 24, and thus it is possible to recognize whether the measurement value measured by the measuring instrument 10 is within an allowable range.

In addition, in one of the present embodiments, whether the measurement value measured by the measuring instrument 10 is within an allowable range is indicated by the coloring of the measurement value indicator 23, and thus it is possible to recognize whether the measurement value measured by the measuring instrument 10 is within an allowable range without occupying the displayable region 24 of the measurement result image 20.

In addition, in one of the present embodiments, the determination result indicator 25 indicating whether the measurement value measured by the measuring instrument 10 is within an allowable range with coloring is displayed outside of the displayable region 24, and thus it is possible to recognize whether the measurement value measured by the measuring instrument 10 is within an allowable range without occupying the displayable region 24 of the measurement result image 20.

In addition, in one of the present embodiments, coloring is linearly changed in accordance with a distance between the display positions of the allowable upper limit value indicator 21 or the allowable lower limit value indicator 22 and the measurement value indicator 23, and thus it is possible to visually discriminate a difference between an allowable value and the measurement value of each measurement item measured by the measuring instrument 10 up to a finer level.

In addition, in one of the present embodiments, in a case of a measurement item having only any one of the allowable upper limit value and the allowable lower limit value, a value separated by a predetermined constant from one allowable value is stored as the other allowable value, and only the allowable upper limit value indicator 21 or only the allowable lower limit value indicator 22 indicating the one allowable value is displayed on the display unit 12. Thereby, even in a case of the measurement item having only any one of the allowable upper limit value and the allowable lower limit value, it is possible to appropriately dispose the measurement value indicator 23.

In addition, in one of the present embodiments, the measurement value indicator 23 is displayed so as to be across the displayable region 24 in a direction intersecting the direction of increase or decrease in numerical value, and thus the region can be intuitively recognized by an operator.

In addition, in one of the present embodiments, the intermediate value indicator 26, and the allowable upper limit value indicator 21 and the allowable lower limit value indicator 22 as positions indicating an allowable upper limit value and an allowable lower limit value are disposed at display positions which are set in advance in the measurement result image 20, the measurement value indicator 23 is disposed at a display position calculated from the display positions of the allowable upper limit value indicator 21 and the allowable lower limit value indicator 22 and the measurement value measured by the measuring instrument 10, and the display of the measurement value display region 27 is changed in accordance with the difference between the display positions of the intermediate value indicator 26 and the measurement value indicator 23. Thereby, it is possible to make a list of how much difference is present between an allowable value and the measurement value of each measurement item measured by the measuring instrument 10 in a discriminable state.

In addition, in one of the present embodiments, only half of a region on a side where the measurement value display region 27 is present in the measurement result image 20 is displayed, and thus it is possible to make a list of how much difference is present between an allowable value and the measurement value of each measurement item measured by the measuring instrument 10, in a more finely and visually discriminable state.

In addition, in one of the present embodiments, the displayable region 24 is displayed in a rectangular shape, or is displayed in a fan shape having a deformed rectangle, and thus the region can be intuitively recognized by an operator.

In addition, in one of the present embodiments, a plurality of measurement result images 20 are arranged and displayed in a lattice shape, and thus it is possible to notice the entire measurement results in perspective.

Meanwhile, in the present embodiment, an example has been described in which the measurement result display device of the present invention is applied to an optical spectrum analyzer device, but the measurement result display device of the present invention can also be applied to other measuring devices such as a logic analyzer device and a spectrum analyzer device.

Hereinbefore, the embodiments of the present invention have been disclosed, but it is obvious that changes and modifications can be made by those skilled in the art without departing from the scope of the present invention. All such modifications and equivalents are intended to be included in the claims.

DESCRIPTION OF REFERENCE NUMERALS AND SIGNS

1: optical spectrum analyzer device (measurement result display device)
10: measurement unit (measuring instrument)
11: storage unit (recording medium)
12: display unit (display device)
13: display control unit
20: measurement result image
21: allowable upper limit value indicator
22: allowable lower limit value indicator
23: measurement value indicator
24: displayable region (frame region)
25: determination result indicator
26: intermediate value indicator
27: measurement value display region
28: allowable value indicator
29: encircling line region
100: measurement result image list

What is claimed is:

1. A measurement result display device comprising:
a display control unit that arranges and displays a plurality of measurement result images indicating measurement results of a plurality of measurement items performed by a measuring instrument, respectively, on a display device; and
a storage unit that has an allowable upper limit value and an allowable lower limit value according to a measurement item stored therein,
wherein, as a measurement result image, the display control unit displays
a frame region,
an allowable upper limit value indicator and an allowable lower limit value indicator that indicate two predetermined positions which are set within the frame region so as to be separated from each other in a first direction across the frame region, as positions indicating the allowable upper limit value and the allowable lower limit value stored in the storage unit, and
a measurement value indicator that indicates a measurement value measured by the measuring instrument, the measurement value indicator being displayed at a position to which the measurement value corresponds with respect to the allowable upper limit value indicator and the allowable lower limit value indicator, with the first direction set to a direction of increase or decrease in numerical value.

2. The measurement result display device according to claim 1,
wherein in a case where the measurement item has only any one of the allowable upper limit value and the allowable lower limit value, the storage unit has a value separated by a predetermined constant from one allowable value stored therein as another allowable value, and
the display control unit displays only the allowable upper limit value indicator or only the allowable lower limit value indicator, indicating the one allowable value, on the display device.

3. The measurement result display device according to claim 1,
wherein the display control unit indicates whether the measurement value is within an allowable range according to the measurement item, with a coloring of the frame region.

4. The measurement result display device according to claim 2,
wherein the display control unit indicates whether the measurement value is within an allowable range according to the measurement item, with a coloring of the frame region.

5. The measurement result display device according to claim 1,
wherein the display control unit indicates whether the measurement value is within an allowable range according to the measurement item, with a coloring of the measurement value indicator.

6. The measurement result display device according to claim 1,
wherein the display control unit further displays a determination result indicator that indicates whether the measurement value is within an allowable range according to the measurement item, as the measurement result image, with coloring, outside of the frame region.

7. The measurement result display device according to claim 3,
wherein the display control unit linearly changes a coloring in accordance with a distance between display positions of the allowable upper limit value indicator or the allowable lower limit value indicator and the measurement value indicator.

8. The measurement result display device according to claim 1,
wherein, as the measurement result image, the display control unit
further displays an intermediate value indicator that indicates an intermediate value between the allowable upper limit value and the allowable lower limit value, the indicator being linearly displayed across a substantial center of the frame region,
linearly displays the allowable upper limit value indicator and the allowable lower limit value indicator across the frame region at both positions having the intermediate value indicator interposed therebetween,
linearly displays the measurement value indicator across the frame region similarly to the intermediate value indicator, and
changes a display of a measurement value display region between the intermediate value indicator and the measurement value indicator, in accordance with a distance between display positions of the intermediate value indicator and the measurement value indicator.

9. The measurement result display device according to claim 8,
wherein the display control unit displays only half of a region on a side where the measurement value display region is present, as the measurement result image.

10. The measurement result display device according to claim 1,
wherein the display control unit displays the measurement value indicator across the frame region in a second direction intersecting the first direction.

11. The measurement result display device according to claim 1,
wherein the display control unit displays the frame region in a rectangular shape, or displays the frame region in a fan shape having a deformed rectangle.

12. The measurement result display device according to claim 1,
wherein the display control unit arranges and displays the plurality of measurement result images in a lattice shape.

13. The measurement result display device according to claim 2,
wherein the display control unit arranges and displays the plurality of measurement result images in a lattice shape.

14. The measurement result display device according to claim 3,
wherein the display control unit arranges and displays the plurality of measurement result images in a lattice shape.

15. The measurement result display device according to claim 4,
wherein the display control unit arranges and displays the plurality of measurement result images in a lattice shape.

16. The measurement result display device according to claim 5,
wherein the display control unit arranges and displays the plurality of measurement result images in a lattice shape.

17. The measurement result display device according to claim 6,
wherein the display control unit arranges and displays the plurality of measurement result images in a lattice shape.

18. The measurement result display device according to claim 8,
wherein the display control unit arranges and displays the plurality of measurement result images in a lattice shape.

19. The measurement result display device according to claim 9,
wherein the display control unit arranges and displays the plurality of measurement result images in a lattice shape.

20. A measurement result display method using a measurement result display device including a display control unit that arranges and displays a plurality of measurement result images indicating measurement results of a plurality of measurement items performed by a measuring instrument, respectively, on a display device, and a storage unit that has an allowable upper limit value and an allowable lower limit value according to the measurement item stored therein, the method comprising causing the display control unit to display a measurement result image in the following steps of:
displaying a frame region;
displaying an allowable upper limit value indicator and an allowable lower limit value indicator that indicate two predetermined positions which are set within the frame region so as to be separated from each other in a first direction across the frame region, as positions indicating the allowable upper limit value and the allowable lower limit value stored in the storage unit; and
displaying a measurement value indicator that indicates a measurement value measured by the measuring instrument, the indicator being displayed at a position to which the measurement value corresponds with respect to the allowable upper limit value indicator and the allowable lower limit value indicator, with the first direction set to a direction of increase or decrease in numerical value.

* * * * *